US006593341B2

(12) United States Patent
Feller et al.

(10) Patent No.: US 6,593,341 B2
(45) Date of Patent: Jul. 15, 2003

(54) β₃-ADRENORECEPTOR AGONISTS, AGONIST COMPOSITIONS AND METHODS OF MAKING AND USING THE SAME

(75) Inventors: Dennis R. Feller, Oxford, MS (US); Duane D. Miller, Germantown, TN (US)

(73) Assignee: Molecular Design International, Inc., Memphis, TN (US)

( * ) Notice: Subject to any disclaimer, the term of this patent is extended or adjusted under 35 U.S.C. 154(b) by 0 days.

(21) Appl. No.: 10/149,953

(22) PCT Filed: Mar. 29, 2001

(86) PCT No.: PCT/US01/10376

§ 371 (c)(1),
(2), (4) Date: Jun. 17, 2002

(87) PCT Pub. No.: WO01/74782

PCT Pub. Date: Oct. 11, 2001

(65) Prior Publication Data

US 2003/0036550 A1 Feb. 20, 2003

(51) Int. Cl.$^7$ ...................... C07D 221/02; A61K 31/47
(52) U.S. Cl. ...................................... 514/307; 546/149
(58) Field of Search .......................... 514/307; 546/149

(56) References Cited

U.S. PATENT DOCUMENTS

| | | | |
|---|---|---|---|
| 3,337,539 A | 8/1967 | Mészáros et al. | |
| 3,438,989 A | 4/1969 | Shavel, Jr. et al. | |
| 3,497,516 A | 2/1970 | Mashimo et al. | |
| 3,647,799 A | 3/1972 | Watanabe et al. | |
| 3,818,015 A | 6/1974 | Yamato et al. | |
| 3,872,130 A | 3/1975 | Kreighbaum et al. | |
| 3,873,704 A | 3/1975 | Yamato et al. | |
| 3,910,915 A | 10/1975 | Yonan | |
| 3,910,927 A | 10/1975 | Kreighbaum et al. | |
| 3,988,339 A | 10/1976 | Kaiser et al. | |
| 4,054,659 A | 10/1977 | Ikezaki et al. | |
| 4,321,254 A | 3/1982 | Ali | |
| 4,442,108 A | 4/1984 | Le Polles et al. | |
| 4,525,589 A | 6/1985 | Hidaka et al. | |
| 4,536,510 A | 8/1985 | Wasserman et al. | |
| 4,666,918 A | 5/1987 | Ivanova et al. | |
| 4,707,485 A | 11/1987 | Kaiser et al. | |
| 4,737,504 A | * 4/1988 | Miller et al. ............... | 514/307 |
| 4,798,897 A | 1/1989 | Hidaka et al. | |
| 4,812,573 A | 3/1989 | Durant et al. | |
| 4,857,301 A | 8/1989 | Czarniecki et al. | |
| 5,059,608 A | 10/1991 | Takasugi et al. | |
| 5,177,085 A | 1/1993 | Naef | |
| 5,210,088 A | 5/1993 | Minchin et al. | |
| 5,238,935 A | 8/1993 | Dugar et al. | |
| 5,246,943 A | 9/1993 | Blankley et al. | |
| 5,272,270 A | 12/1993 | Hirsenkorn et al. | |
| 5,340,811 A | 8/1994 | Kajihara et al. | |
| 5,350,757 A | 9/1994 | Blankley et al. | |
| 5,362,736 A | 11/1994 | Ishikawa et al. | |
| 5,446,164 A | 8/1995 | Ishikawa et al. | |
| 5,498,717 A | 3/1996 | Ishikawa et al. | |
| 5,519,034 A | 5/1996 | Kozlik et al. | |
| 5,525,614 A | 6/1996 | Blankley et al. | |
| 5,707,985 A | 1/1998 | McKenzie et al. | |
| 5,750,520 A | 5/1998 | Danilewicz et al. | |
| 5,756,516 A | 5/1998 | Liu et al. | |
| 5,798,352 A | 8/1998 | Danilewicz | |
| 5,804,586 A | 9/1998 | Sargent et al. | |
| 5,807,868 A | 9/1998 | Sargent et al. | |
| 5,880,285 A | 3/1999 | Broger et al. | |
| 5,929,085 A | 7/1999 | MacDonald et al. | |
| 6,043,253 A | 3/2000 | Brockunier et al. | |
| 6,063,925 A | 5/2000 | Demian et al. | |
| 6,127,381 A | 10/2000 | Basu et al. | |
| 6,153,608 A | 11/2000 | Hidaka et al. | |
| 6,248,754 B1 | 6/2001 | Coulton et al. | |
| 6,274,594 B1 | 8/2001 | Coulton et al. | |
| 6,277,861 B1 | 8/2001 | Harling et al. | |
| 2001/0039285 A1 | 11/2001 | Cameron et al. | |
| 2001/0039289 A1 | 11/2001 | Blok et al. | |

FOREIGN PATENT DOCUMENTS

| | | | |
|---|---|---|---|
| EP | 0 210 827 A2 | 2/1987 | |
| JP | 47018898 | 9/1972 | |
| JP | 52095676 | 8/1977 | |
| WO | WO 99/16752 | * 4/1999 | ......... C07D/221/02 |
| WO | WO 99/44609 A1 | 9/1999 | |

OTHER PUBLICATIONS

Parmee et al, Bioorganic & Medicinal Chemistry, vol. 10, No. 20, pp. 2283–2286, 2000.*

Adejare, et al., "Syntheses and β–Adrenergic Agonist and Antiaggregatory Properties of N–Substituted Trimetoquinol Analogues¹", *J. Med. Chem.*, 1986, pp. 1603–1609, vol. 29.

Ahn, et al., "Characterization of the Inhibition of U46619–Mediated Human Platelet Activation by the Trimetoquinol Isomers", *Biochemical Pharmacology,* 1988, pp. 3023–3033, vol. 37, No. 15.

Christoff, et al., "Synthesis and Evaluation of Trimetoquinol Derivatives: Novel Thromboxane A₂/Prostaglandin H₂ Antagonists with Diminished β–Adrenergic Agonist Activity", *J. Med. Chem.*, 1997, vol. 40, pp. 85–91.

Clark, et al., "5–Fluoro– and 8–Fluorotrimetoquinol: Selective β₂–Adrenoceptor Agonists", *J. Med. Chem.,* 1987, pp. 86–90, vol. 30.

De Los Angeles, et al., "Iodinated Analogs of Trimetoquinol as Highly Potent and Selective β₂–Adrenoceptor Ligands", *J. Med. Chem.,* 1996, vol. 39, pp. 3701–3711.

(List continued on next page.)

*Primary Examiner*—Zinna Northington Davis
(74) *Attorney, Agent, or Firm*—Alston & Bird LLP

(57) ABSTRACT

The invention provides compounds useful as β₃-adrenorecptor agonists and pharmaceutical compositions comprising such compounds. The invention further includes a method for stimulating, regulating, and modulating metabolism in fats of adipose tissue in mammals by administering an effective amount of a compound of the invention.

73 Claims, No Drawings

OTHER PUBLICATIONS

Fraundorfer, et al., "Biochemical and Pharmacological Characterization of High–Affinity Trimetoquinol Analogs on Guinea Pig and Human Beta Adrenergic Receptor Subtypes: Evidence for Partial Agonism[1]", *J. Pharmacology and Experimental Therapeutics*, 1994, pp. 665–674, vol. 270, No. 2.

Fraundorfer, Paul F., "Functional and Biochemical Characterization of Trimetoquinol (TMQ) Analog Interactions with β–Adrenergic Receptor Subtypes", A Dissertation, The Ohio State University, 1993.

Gavai, et al. "BMS–196085: A Potent and Selective Full Agonist of the Human $β_3$ Adrenergic Receptor", *"Bioorg. Med. Chem. Lett."*, 2001, pp. 3041–3044, vol. 11.

Harrold, et al., "Synthesis and Platelet Antiaggregatory Activity of Trimetoquinol Analogs as Endoperoxide/Thromboxane $A_2$ Antagonists", *Drug Design and Delivery*, 1987, pp. 193–207, vol. 1.

He, et al., "Synthesis and Human β–Adrenoceptor Activity of 1–(3,5–Diiodo–4–methoxybenzyl)–1,2,3,4–tetrahydroisoquinolin–6–ol Derivatives In Vitro", *J. Med. Chem.*, 2000, pp. 591–598, vol. 43, No. 4.

He, et al., "Synthesis and Human β–Adrenoceptor Activity of 1,2,3,4–Tetrahydroisoquinoline–6–ol Derivatives, In Vitro", *Am. Chem. Soc.*, 218th ACS National Meeting, Aug. 22–26, 1999, Abstract.

Howe, Ralph, "$β_3$–Adrenergic agonists", *Drugs of the Future*, 1993, pp. 529–549, vol. 18, No. 6.

Hu, et al., "(4–Piperidin–1–yl)phenyl Amides: Potent and Selective Human $B_3$ Agonists", *J. Med. Chem.*, 2001, pp. 1456–1466, vol. 44, No. 9.

Ishiwata, et al., "Synthesis of Aminoisoquinolines and Related Compounds. IX. Synthesis of (+−)–0–methylcaseadine", *Chem. Pharm. Bull.*, 1970, vol. 18(9), Abstract.

Ishiwata, et al., "Syntheses of Aminoisoquinolines and Related Compounds. VI. A Modified Synthesis of dl–pronuciferine", *Chem. Pharm. Bull.*, 1970, vol. 18(6), Abstract.

Ishiwata, et al., "Syntheses of Aminoisoquinolines and Related Compounds. II. Syntheses of 6–amino–1–benzylisoquinolines by the Bischler–Napieralski reaction", *Chem. Pharm. Bull.*, 1969, vol. 17(11), Abstract.

Iwasawa, et al., Studies on Tetrahydroisoquinolines (THI) (I) Bronchodilator Activity an Structure–Activity Relationship, *Jap. J. Pharmacol.*, 1967, pp. 143–152, vol. 17.

Kajigaeshi, et al., Halogenation Using Quaternary Ammonium Polyhalides. VII. [1)] Iodination of Aromatic Amines by Use of Benzyltrimethylammonium Dichloroiodate(1−), *Bull. Chem. Soc. Jpn.*, 1988, pp. 600–602, vol. 61, No. 2.

Mayo, et al., "Stereo–Dependent Inhibition of Human Platelet Function by the Optical Isomers of Trimetoquinol", *Biochemical Pharmacology*, 1981, pp. 2237–2241, vol. 30, No. 16.

Memetzidis, et al., "Synthesis of Aromatic Chloroberbines", *Heterocycles*, 1990, vol. 31(2), Abstract.

Mehta, et al., "Biochemical and Functional Characterization of 1–Benzyl Substituted Trimetoquinol Affinity Analogs on Rat and Human β–Adrenoceptors," *Biochemical Pharmacology*, 2000, pp. 517–529, vol. 59.

Nikulin et al., "A Shortened Approach to Parallel Synthesis of Tetrahydroisoquinolines (THI) Via Bishler–Napieralski Cyclization", *Am. Chem. Soc.*, 215th ACS National Meeting, Mar. 29–Apr. 2, 1998.

Nikulin, et al., "7–Substituted 1–Aryl–1,2,3,4–tetrahydroisoquinolin–6–ols as Selective Agonists for Human $β_3$–Adrenoceptor", *Am. Chem. Soc.*, 219th ACS National Meeting, Mar. 26–30, 2000.

Shin, et al., "Interactions of Nonprostanoid Trimetoquinol Analogs with Thromboxane $A_2$/Prostaglandin $H_2$ Receptors in Human Platelets, Rat Vascular Endothelial Cells and Rat Vascular Smooth Muscle Cells[1]", *J. Pharmacology and Experimental Therapeutics*, 1993, pp. 1017–1023, vol. 267, No. 3.

Shin, et al., "Stereospecific Interactions of Nonprostanoid Trimetoquinol Analogs With Thromboxane $A_2$/Prostaglandin $H_2$ Receptor Sites in Human and Rat Platelets, and Rat Vascular Endothelial and Smooth Muscle Cells", *Pharmacology Communications*, 1992, pp. 303–312, vol. 1, No. 4.

Shin, et al., "Pharmacologic Antagonism of Thromboxane $A_2$ Receptors by Trimetoquinol Analogs In Vitro and In Vivo", *Chirality*, 1991, pp. 112–117, vol. 3.

Washburn, et al. "Beta 3 Agonists. Part 1: Evolution from Inception to BMS–19449", *"Bioorg. Med. Chem. Lett."*, 2001, pp. 3035–3039, vol. 11.

Yamato, et al., "Synthesis of 6,7–Dihydroxy–1,2,3,4–Tetrahydroisoquinoline Derivatives", *Tetrahedron*, 1966, pp. 129–134, Suppl. 8, Part 1.

Zheng, et al. "2–Amino–4–benzyl–4,5,6,7–tetrahydrothiazolo[5,4–c]pyridines: Novel Selective $β_3$–Adrenoceptor Agonists", *J. Med. Chem.*, 1999, pp. 2287–2294, vol. 42, No. 12.

Zheng, et al., "2–Amino–4–Aryl–4,5,6,7–Tetrahydrothiazolo[5,4–c]Pyridines: Proposed Novel Catechol Bioisosteric Analogs of Trimetoquinol (TMQ)—A Potent β–Adrenoceptor Agonist and TP Receptor Antagonist", *Am. Chem. Soc.*, 1995 Joint Southeast–Southwest Regional Meeting, Nov. 29–Dec. 1, 1995, Abstract.

\* cited by examiner

β₃-ADRENORECEPTOR AGONISTS, AGONIST COMPOSITIONS AND METHODS OF MAKING AND USING THE SAME

CROSS-REFERENCE TO RELATED APPLICATIONS

This application is a 35 U.S.C. §371 national phase application corresponding to PCT/US01/10376 filed Mar. 29, 2001, which is hereby incorporated by reference herein in its entirety.

BACKGROUND

1. Technical Field

The present invention relates to the field of $\beta_3$-Adrenoreceptor agonists and to methods of their preparation, formulation and use to stimulate, regulate and modulate metabolism of fats in adipose tissues in animals, particularly humans and other mammals. More particularly, the present invention relates to the field of treating obesity and overweight conditions in animals, particularly humans and other mammals and associated effects of conditions associated with obesity and overweight, including Type II diabetes mellitus (non-insulin dependent diabetes), insulin resistance, glucose intolerance, hypothyroidism, morbid obesity, and the like.

2. Prior Art

It was long thought that obesity was a consequence of self-indulgence and undisciplined behavior. Obesity was seen as evidence of gluttony, through a lack of will or capacity for self-discipline The overweight have been disparaged, and thinness has been celebrated. Indeed, the perception of thinness as a major aspect of human beauty and attractiveness has become endemic in modern culture, and overweight conditions and obesity has increasingly grown to be an unacceptable condition for social reasons.

Masked by these cultural icons are the hard medical facts: for many individuals, a tendency to overweight and even obesity are often symptoms of organic disease or disorders of the metabolism, associated with serious and even life-threatening conditions. In medical economic terms alone, the costs attributable to overweight and obesity are staggeringly high.

A wide variety of approaches to the alleviation of obesity have ebbed and flowed though modern culture, ranging from a diverse collection of dietary strategies, to drugs, to surgical interventions, to hypnosis. All have met with indifferent success at best. Some have proved to be outright quackery. Others have proved to be effective only for the short-term, with loss of effectiveness over time. Still others have proved to be generally or at least partially successful so long as the regimen is sustained, but long term compliance is difficult to attain and in some cases has proved hazardous to other aspects of health and well-being. Some surgical procedures have had some successes, but as with any invasive procedures, there are risks. Some approaches to weight loss and control, in the extreme, lead to conditions which are themselves pathological, such as bulimia and anorexia nervosa. Other effects are less extreme, but still highly undesirable, such as amennorhea, vitamin and essential nutrient deficiencies, and the like.

A great deal of the difficulty in the art and practice of obesity and overweight management has been a consequence of attention focused on the control of appetite, and reducing the amount of food intake. It has long been the belief of many that only by the control of caloric intake is it possible to regulate body weight and fat deposition and utilization. Since appetite is controlled and regulated in the brain, brain pharmacology and the alteration of brain chemistry has been a primary focus of weight regulation and control efforts. Such approaches have led to addictions to appetite suppressants, to primary pulmonary myopathy, cardiac valve damage, and to reports of serotonin disruptions and disorders and psychotic episodes among users. Morbities and mortalities have been unacceptably high.

In another aspect of technology relating to fat is the dietary emphasis on limiting dietary fat intake. For those who eat meats, there is increasing emphasis on low fat content meats in the carcasses of the animals employed in food stocks. Much recent efforts have been devoted to the production of beef, pork, poultry and the like with reduced fat content. Breeding patterns are being manipulated and generic engineering of farm animals is being directed at lowering fat content of the animals. The techniques of fattening of animals intended for table meat production is highly developed, but is gradually being limited by the emphasis on limiting dietary fats and interest in leaner carcass animals.

Only in very recent times has obesity been addressed in relation to the metabolic pathways of the body and their role and import in fat storage and usage in the body.

Recent research has elucidated some of the mechanisms of obesity and overweight, and has revealed that much of the limitation of prior and current weight-loss techniques stems from the fact that they are biochemically and particularly metabolically unsound and incapable of stimulating, regulating and modulating metabolism of fats in adipose tissues. Without these characteristics, it is now known, weight loss and control strategies are likely to fail or to produce conditions as bad as or worse than the weight problems they are intended to alleviate. Without heroic dedication and discipline, and even fanaticism, by the subject, most strategies are short term in their weight loss and control effects.

Increasing efforts have been directed to biochemical research into the mechanisms of fat deposition and metabolism and into stimulating, regulating and modulating metabolism of fats in adipose tissues. Considerable recent progress has been made.

Among the biochemical work of note has been the recent recognition of a role of β-Adrenoreceptor activity in the metabolism of fats. It has been recognized that agonists for β-Adrenoreceptors have, in some cases, produced marked weight loss in animals, particularly humans and other mammals.

More recently, the loss of weight has been identified with the β-Adrenoreceptor sub-type, $\beta_3$-Adrenoreceptors. The specific structure of the $\beta_3$-Adrenoreceptor has not been characterized, but it has been demonstrated to be a distinct cellular structure, distinguishable from the $\beta_1$-Adrenoreceptor and the $\beta_2$-Adrenoreceptor sites previously identified.

It has been demonstrated that compounds which are significant $\beta_3$-Adrenoreceptor agonists produce marked weight loss in animals, particularly humans and other mammals, and that the loss is sustained with continuation of the administration of such compounds. These compounds provide potent regulation of fat metabolism. The compounds employed to date are also agonists for the $\beta_1$-Adrenoreceptor and the $\beta_2$-Adrenoreceptor sites. The lack of selectivity represents unwanted side effects of such compounds, and the compounds known as $\beta_3$-Adrenoreceptor agonists to date are not suitable candidates for therapeutic usage because of the unwanted and dangerous side effects.

3. Problems and Needs in the Art

The existing strategies for weight and body fat regulation are inadequate. The current strategies are ineffective, unsafe, or both. Whether through diet manipulations or through drug usage, or combinations of such strategies, there is a lack of a clear path to safe and effective regulation of body weight and body fat which is safe and effective, which can provide significant and long lasting relief from the health consequences of overweight and obesity and the conditions associated therewith, and from the disease conditions which are aggravated by overweight and obesity.

It is clear that the art lacks and needs therapeutic agents which are highly potent and highly selective $\beta_3$-Adrenoreceptor agonists for effective stimulation, regulation and modulation of metabolism of fats in adipose tissues.

It is also clear that the art lacks and needs agents which are effective $\beta_3$-Adrenoreceptor agonists free of unwanted side effects, and which are safe for stimulating, regulating and modulating metabolism of fats in adipose tissues.

It is clear that the art lacks and needs agents which are effective at regulating the body fat of animals, particularly humans and other mammals, both in the reduction of body weight in the obese and the attendant health problems and issues, and in the production of low fat table meats from domesticated animals for human consumption.

OBJECTS OF THE INVENTION

It is an object of the present invention to provide novel compounds which are safe and effective $\beta_3$-Adrenoreceptor agonists.

It is another object of the present invention to provide syntheses of such $\beta_3$-Adrenoreceptor agonists.

Another object of the present invention is the provision of safe and effective $\beta_3$ Adrenoreceptor formulations for administration to stimulate, regulate and modulate metabolism of fats in adipose tissues in animals, particularly humans and other mammals.

Still another object of the present invention is to provide safe and effective administration of $\beta_3$-Adrenoreceptor agonists for stimulating, regulating and modulating metabolism of fats in adipose tissues in animals, particularly humans and other mammals.

Yet another object of the present invention is to provide a safe and effective regimen for causing and promoting weight loss in humans, and for the maintenance of healthy and personally desired body fat levels.

Still another object of the present invention is to provide safe and effective adjuncts to the husbandry of domesticated animals for the production of low fat dietary meats for human consumption.

The primary objective of the present invention is to provide for weight and body fat regulation through modalities which are effective and safe. The present invention provides a clear path to safe and effective regulation of body weight and body fat which is safe and effective, which can provide significant and long lasting relief from the health consequences of overweight and obesity and the conditions associated therewith, and from the disease conditions which are aggravated by overweight and obesity.

These and related objectives are met by the terms of the present invention as set out in detail in the following specification and defined in the claims appended hereto.

SUMMARY OF THE INVENTION

Compounds which are highly potent and highly specific $\beta_3$-Adrenoreceptor agonists are provided. The compounds are formulated into pharmaceutical preparations and administered for stimulating, regulating and modulating metabolism of fats in adipose tissues in animals, particularly humans and other mammals.

The compounds of the invention have the structure:

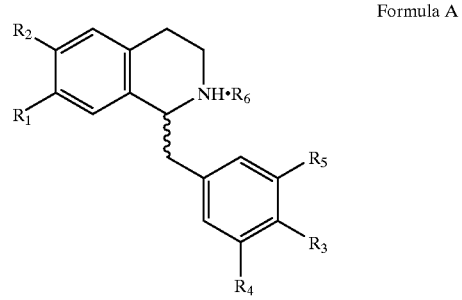

Formula A $R_1$ and $R_2$ are each independently members selected from the group consisting of H, OH, Cl, $NO_2$, $CH_3SO_2NH$, $NH_2$, $CH_3O$ and weak acids of the structure $R_7$—NH, where $R_7$ is an acyl group, wherein at least one of $R_1$ and $R_2$ is OH. It is generally preferred that $R_2$ be OH.

$R_3$, $R_4$ and $R_5$ are variously and independently members selected from I, Br, Cl, F, $OCH_3$, $CH_3$, alkyl, alkylaryl, aminoalkyl, thioalkyl, and O-alkyl. Preferably, R4 and R5 are each a halogen, the same or different.

$R_6$ is an acid moiety which forms an acid salt with the NH group. $R_6$ is desirably HCl or $(COOH)_2$.

While the racemic mixtures are active, selective, and bioavailable, we have found that the isolated isomers are ordinarily of more particular interest. The S(−) isomers are preferred, as they will be found to have the highest selectivity and the highest bioavailability. The R(+) isomers are also of interest, as the R-isomers are in some cases easier to isolate.

The compounds are formulated into pharmaceutical carriers to serve as highly selective, effective and safe $\beta_3$-Adrenoreceptor agonists to provide long term weight control.

In humans, the compositions are administered to control body fat levels, and to maintain acceptable body fat levels over time.

In domesticated animals, the compositions are administered to attain desirably low fat content in carcass meats intended for human consumption.

DETAILED DESCRIPTION

In the following description of the invention, the compounds of the present invention, the method of their synthesis, their formulation into pharmaceutical compositions suitable for administration, and the method of their use for stimulating, regulating and modulating metabolism of fats in adipose tissues in animals, particularly humans and other mammals.

The discussion and presentation of bioactivity information and data in the present description is made in compliance with the standards of the Journal of Medicinal Chemistry. All chemical compounds are named in accordance with the standards of the American Chemical Society rules of standard nomenclature, employing accepted "trivial names"

where applicable. All chemical structures are shown in "skeletal" form, for clarity in understanding the most significant considerations and information about the structures, with implicit hydrogen atoms not relevant to the conformation of structures not shown, in the fashion typically employed in the Journal of Medicinal Chemistry and many other journals of chemistry. The use of such structural notation is most convenient to understand the structures of such molecules, and those of ordinary levels of skill in the relevant arts are accustomed to such representations and are readily able to identify and understand such "skeletal" structures, including the implicit hydrogen atoms not shown.

Introduction

The risks and unacceptable levels of adverse consequences of many weight control and weight loss strategies available to individuals and to the medical community make the development of safe and effective modalities for stimulating, regulating and modulating metabolism of fats in adipose tissues an important need in the art and in society as a whole.

The importance of regulating dietary fat intake, and particularly saturated animal fat, has long been recognized. Consumption of meats is primary in the diet in most developed countries, and substantial efforts have been devoted to the development of leaner animals, among other strategies, to facilitate regulating and limiting of dietary intake of saturated animal fats.

In the present invention, the highly desirable goals of stimulating, regulating and modulating metabolism of fats in adipose tissues in animals, particularly humans and other mammals through the modality of administering a pharmaceutical formulation of one or more compounds which are $\beta_3$-Adrenoreceptor selective agonists is provided.

The regulatory and modulatory effect of the compounds of the present invention are dependent on continued administration over time, and the attainment of an equilibrium state which is believed to be dose dependent. In that fashion, the present invention affords the control of body fat in animals, particularly humans and other mammals, over sustained periods, at desirable levels of body fat and/or body mass indices, as defined in the medical literature.

Overview of the Invention

Safe and effective control of body fat and body mass indices have been a long sought but quite elusive goal for the medical community. The modalities in use over the past half century have proved to be both dangerous and limited in effectiveness. The longer the effort is sustained, in general, the higher the risk and the lower the effectiveness.

The weight loss effect of β-Adrenoreceptor agonists generally has been known per se for a considerable period. That recognition has not led to safe and effective weight loss or regulation because of the copious and highly dangerous side effects.

The recent discovery of the $\beta_3$-Adrenoreceptor and its focal role in fat metabolism holds the promise of the employment of $\beta_3$-Adrenoreceptor agonists in weight loss and regulation. Through the development of compounds which are highly selective for the $\beta_3$-Adrenoreceptor without activation of the $\beta_1$ Adrenoreceptor and $\beta_2$ Adrenoreceptor the present invention makes that goal attainable.

The $\beta_3$-Adrenoreceptor has not been characterized to date, which makes the search for safe and effective agonists with the required high selectivity a difficult and arduous task. Without a clear understanding of the receptor binding site, the design of effective compounds is based largely on structural activity correlations which are uncertain, unpredictable and unreliable. Even the most minor changes in structure can produce wide deviations in binding affinity, binding specificity, and agonist activity. The compounds of the present invention attain the high affinity for the $\beta_3$-Adrenoreceptor, the low affinity for the $\beta_1$ Adrenoreceptor and the $\beta_2$ Adrenoreceptor required for effective selectivity and freedom from adverse side effects, and high levels of agonist activity to make the compounds effect in their required role in fat metabolism.

THE β-ADRENORECEPTOR FAMILY

β Adrenoreceptors have long been known and have been studied for their role in response to the catechol amine hormones adrenaline (epinephrine), noradrenaline (norepinephrine) and dopamine.

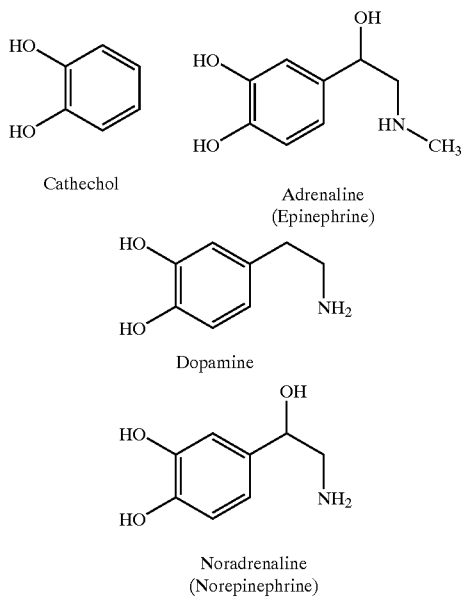

Cathechol

Adrenaline (Epinephrine)

Dopamine

Noradrenaline (Norepinephrine)

Adrenaline, to exemplify the biochemical action of these catechol amine hormones, is a primary agonist for these receptors in the body, and activates metabolic processes within the cells to which it binds. Adrenaline is associated with specific cellular processes which are dependent upon the nature of the cell to which it is bound. The action of adrenaline on the cell is to activate an enzyme within the cell, adenylate cyclase. The adenylate cyclase in turn catalyses further reactions within the target cell, typically beginning an enzyme cascade until the enzyme is broken down or deactivated by cellular regulatory mechanisms. The primary action of adenylate cyclase is the conversion of ATP to cAMP (cyclic adenosine monophosphate or "cyclic adenylate").

In the liver cells, the cAMP activates, in turn, an enzyme cascade which catalyses the conversion of glycogen into glucose and inhibits the conversion of glucose into glycogen, greatly increasing extra-cellular levels of blood glucose in the body.

In muscle tissues, cAMP triggers the breakdown of glycogen into lactate and ATP, providing high levels of ATP to support high levels of muscular activity. In the heart muscle, in particular, the effect is hypertensive and is accompanied by vasodilation throughout the body, increasing blood flow and transport of blood glucose to the cells.

(β-blockers are among the commonly prescribed drugs in the field of cardiology. For the hypertensive patient, competitive binding of the blocking agent to the β Adrenoreceptors modulates and limits the additional hypertensive action of adrenaline on the heart muscle. The β-blockers may be employed in combination with vasodilators, decreasing the resistance to blood flow peripherally without increasing the heart rate and strength of contraction. A reduction in blood pressure and the work requirement on the heart muscle results.)

In the lung, cAMP acts to cause bronchodilation which, when combined with increased blood flow, supplies higher levels of oxygen transport.

(Adrenaline, or epinephrine, is widely employed to stimulate bronchodilation in the treatment of asthma and allergenic reactions which constrict the bronchia.)

Others of the catechol amine hormones have comparable activities.

The release of free fatty acids from adipose tissue has been observed as an action provided by β Adrenoreceptor agonists.

A variety of β Adrenoreceptor agonists and blockers have been known for some time, and have proved to be a fruitful field for drug development.

It has been recognized that there are sub-types of the β Adrenoreceptor, designate the $\beta_1$ Adrenoreceptor and the $\beta_2$ Adrenoreceptor. Lands, et al., "*Differentiation of Receptor Systems Activated by Sympathomimetic Amines*" Nature, 214:597–598 (1967). Lands, et al., associate the release of free fatty acids from adipose tissue with $\beta_1$ Adrenoreceptor activation.

Subsequent studies have provided a spectrum of β Adrenoreceptor agonists and blockers. Among the blockers are both competitive and non-competitive (non-equilibrium) binding agents. Some of such agents are ubiquitous in their action, while others exhibit varying degrees of selectivity for the two sub-types (and hence in the action response produced).

Selective agonist studies show both qualitative and quantitative differentiation of the sub-types. $\beta_1$ Adrenoreceptor activation have been demonstrated to cause cardiac stimulation, release of free fatty acids from adipose tissue, and intestinal inhibition. In contrast, $\beta_2$ Adrenoreceptor activation produces broncho- and vaso-dilation.

THE $\beta_3$-ADRENORECEPTOR

Quite recently, a third sub-type of the β Adrenoreceptor family has been identified. Howe, R. "*Beta-3 adrenergic agonists.*" Drugs Future 1993, 18, 529–549. It has been designated the $\beta_3$ Adrenoreceptor. It has also been specifically identified with the release of free fatty acids from adipose tissue, previously attributed by Lands et al. with the $\beta_1$ Adrenoreceptor.

While $\beta_1$ Adrenoreceptor and $\beta_2$ Adrenoreceptor sites are ubiquitous, it has been found that the $\beta_3$-Adrenoreceptor sites are more specialized and are predominantly located on adipose tissue cells, and from studies to date appear to be rather specifically associated with the metabolism of fats.

$\beta_3$-ADRENORECEPTOR AGONISTS

This discovery leads quite directly to the search for selective and potent agonists for the $\beta_3$ Adrenoreceptor for the treatment of obesity and control of weight. The search is hindered by the lack of characterization of the receptor, but the information from binding studies and other work on β Adrenoreceptor agonists generally indicates that $\beta_3$ Adrenoreceptor agonists should be similar in structure to the catechol amine hormones.

Rather little has been published to date on $\beta_3$ Adrenoreceptor agonists. See, however, Howe, R. "Beta-3 adrenergic agonists" *Drugs Future* 1993, 18, 529–549. It is accordingly necessary to extrapolate from the information available about $\beta_1$ Adrenoreceptor and $\beta_2$ Adrenoreceptor agonists, and to engage in an attempt to discern structural and activity relationships from the available data. The following comments on $\beta_1$ Adrenoreceptor and $\beta_2$ Adrenoreceptor considerations summarizes what is known in the literature upon which the effort to develop $\beta_3$-Adrenoreceptor agonists can be based.

Trimetoquinol is a potent nonspecific β-adrenoceptor (β-AR) agonist clinically used in Japan as a bronchorelaxant. Iwasawa, Y.; Kiyomoto, A. "Studies of tetrahydroisoquinolines (THI) 1. Bronchodilator activity and structure-activity relationships." *Jap. J. Pharmacol.* 1967, 17, 143–152. Optical resolution of trimetoquinol and subsequent evaluation of the stereoisomers revealed that the (S)-(−)-isomer of trimetoquinol is a potent β-adrenoceptor agonist in heart and lung tissues; whereas, the (R)-(+)-isomer acts as a selective and highly stereospecific TP receptor antagonist. Yamamoto, E.; Hirakura, M.; Sugasawa, S. "Synthesis of 6,7-dihydroxy-1,2,3,4-tetrahydroisoquinoline derivatives" *Tetraheron Suppl.* 1966, 8 (Part 1), 129–134. Mayo, J. R.; Navaran, S. S.; Akbar, H.; Miller, D. D.; Feller, D. R. "Stereodependent inhibition of human platelet function by the optical isomers of trimethoquinol" *Biochem. Pharmacol.* 1981, 30, 2237–2241. Ahn, C. H.; Romstedt, K. J.; Wallace, L. J.; Miller, D. D.; Feller, D. R. "Characterization of the inhibition of U46619-mediated human platelet activation by the trimetoquinol isomers. Evidence for endoperoxide/thromboxane $A_2$ receptor blockade" *Biochem Pharmacol* 1988, 37, 3023–33. Shin, Y.; Romstedt, K. J.; Miller, D. D.; Feller, D. R. "Stereodependent antagonism of thromboxane $A_2$/prostaglandin $H_2$ receptor sites by trimetoquinol isomers in human platelets, rat vascular endothelial cells and rat vascular smooth muscle cells" *Pharmacol. Commun.* 1993, 1, 303–312. Radioligand competition binding studies at β-adrenoceptor and TP receptors show high stereoselective binding (>100-fold) for the S(−)-isomer and R(+)-isomer, respectively. This stereoselectivity is also observed in the binding of fluorinated trimetoquinol analogs at β-adrenoceptor. Clark, M. T.; Adejare, A.; Shams, G.; Feller, D. R.; Miller, D. D. "5-fluoro- and 8-fluorotrimetoquinol: selective beta 2-adrenoceptor agonists" *J Med Chem* 1987, 30, 86–90.

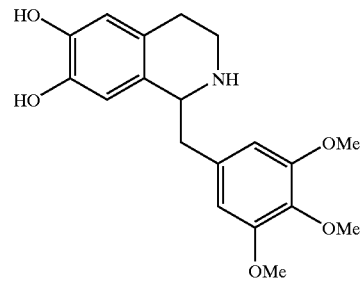

Trimetoquinol

The basic catechol structure of catecholamine hormones, such as epinephrine, norepinephrine, dopamine, and the β-adrenoceptor agonist isoproterenol, is incorporated within the tetrahydroisoquinoline nucleus of trimetoquinol. In studies using mutated hamster $\beta_2$ Adrenoreceptor expressed in Chinese hamster ovary (CHO) cells, replacement of Asp113 with Asn113 abolished receptor binding of trimetoquinol and its analogs. Fraundorfer, P. F. "Functional and biochemical Characterization of trimetoquinol (TMQ) analog interactions with β-adrenergic receptor subtypes" Ph. D. Thesis, The Ohio State University, 1993 ("Fraundorfer-2"). In addition, replacement of Ser204 and Ser207 with Ala204 and Ala207 decreased the binding affinity of trimetoquinol analogs in $\beta_2$ Adrenoreceptor to a lesser extent, but greatly diminished their ability to stimulate cAMP accumulation. "Fraundorfer-2", supra. However, both the binding and functional activities of isoproterenol are significantly reduced in the $\beta_2$ Adrenoreceptor Asn113, Ala204 and Ala207 mutants. These results suggest that although trimetoquinol analogs may interact with the same amino acid residues in the binding site as isoproterenol, the contribution of catechol interactions with these mutated $\beta_2$ Adrenoreceptors is less significant in terms of ligand binding and may well be overshadowed by the binding contributions of the trimethoxybenzyl group of trimetoquinol.

Substitution with fluorine or iodine on the 5- or 8-positions of trimetoquinol resulted in only a modest (~10-fold) increase in $\beta_2$ Adrenoreceptor versus $\beta_1$ Adrenoreceptor selectivity as compared to trimetoquinol in functional and binding studies. Clark, et al., supra; Fraundorfer, P. F.; Fertel, R. H.;. Miller, D. D.; Feller, D. R. "Biochemical and pharmacological characterization of high-affinity trimetoquinol analogs on guinea pig and human beta adrenergic receptor subtypes: evidence for partial agonism" *J Pharmacol Exp Ther* 1994, 270, 665–74.. In addition, it has also found that replacement of the 3'- and 5'-methoxy substituent of trimetoquinol with iodine atoms (i.e., 2) is well tolerated on both β-adrenoceptor, Fraundorfer, et al., supra, and TP receptors. Shin, Y.; Romstedt, K. J.; Miller, D. D.; Feller, D. R. "Interactions of nonprostanoid trimetoquinol analogs with thromboxane A$_2$/prostaglandin H$_2$ receptors in human platelets, rat vascular endothelial cells and rat vascular smooth muscle cells" *J Pharmacol Exp Ther* 1993, 267, 1017–23.; Harrold, M. W.; Gerhardt, M. A.; Romstedt, K.; Feller, D. R.; Miller, D. D. "Synthesis and platelet antiaggregatory activity of trimetoquinol analogs as endoperoxide/thromboxane A2 antagonists" *Drug Des Deliv* 1987, 1, 193–207.

Interestingly, although its binding affinity at $\beta_1$ Adrenoreceptor is slightly better than trimetoquinol, compound 2 displays a much higher affinity than trimetoquinol for $\beta_2$ Adrenoreceptor:

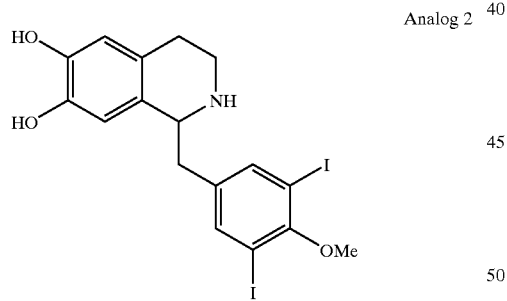

Analog 2

These earlier findings suggest that trimetoquinol analogs interact with an auxiliary site through the substituted benzyl group in addition to the binding site shared by catecholamines. This subsite can be used to advantage in the development of more site-selective agents. The high potency of compound 2 seems to suggest that this auxiliary site is hydrophobic in nature. On TP receptors, the complementary binding sites for trimetoquinol analogs are essentially unknown. However, compound 2 is a more potent TP receptor antagonist than trimetoquinol further suggesting that 1-benzyl ring modifications are appropriate to develop agents with greater selectivity on β-Adrenoreceptor versus TP receptors and vice versa.

The literature describes the synthesis and evaluation of iodinated trimetoquinol analogs designed as probes for characterizing the receptor binding interactions, associated with the benzyl substituent of trimetoquinol analogs and as site-selective β-adrenoceptor and TP ligands. These chemical modifications provide a greater separation of the pharmacological activities for this class of compounds. Site-selective β-adrenoceptor agents have potential in the treatment of cardiopulmonary diseases, non-insulin dependent diabetes (Type II) and obesity, Howe, R., "Beta-3 adrenergic agonists" *Drugs Future* 1993, 18, 529–549, whereas highly selective TP receptor antagonists have value in the treatment of thrombolytic disorders. Shin, supra; Shin, Y.; Romstedt, K. J.; Miller, D. D.; Feller, D. R., "Interactions of nonprostanoid trimetoquinol analogs with thromboxane A$_2$/prostaglandin H$_2$ receptors in human platelets, rat vascular endothelial cells and rat vascular smooth muscle cells" *J Pharmacol Exp Ther* 1993, 267, 1017–23; Shin, Y.; Romstedt, K; Doyle, K.; Harrold, M.; Gerhardt, M.; Miller, D.; Feller, D., "Pharmacologic antagonism of thromboxane A$_2$ receptors by trimetoquinol analogs." *Chirality* 1991, 3, 112–117.

Other known $\beta_1$ Adrenoreceptor and $\beta_2$ Adrenoreceptor agonists include Isoproterenol, X and Y, having the structures:

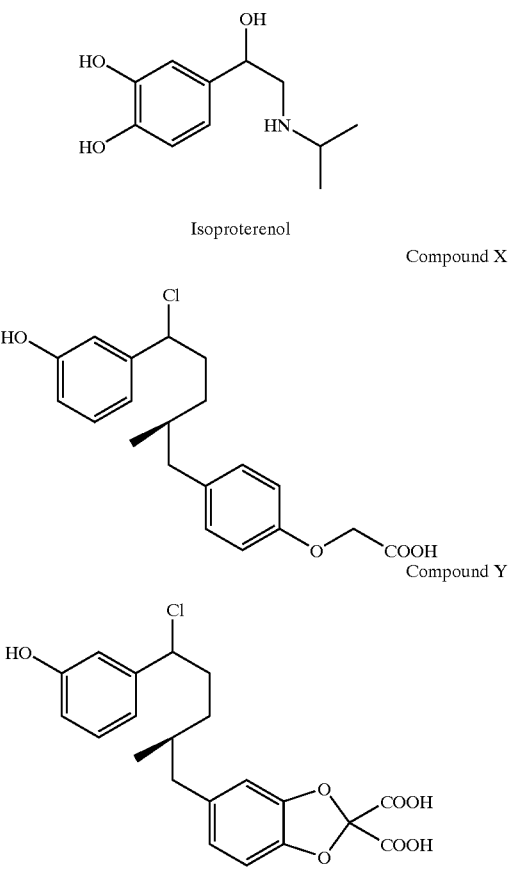

While these compounds are highly active $\beta_3$-Adrenoreceptor agonists, they are also non-selective, and also bind and activate the $\beta_1$ Adrenoreceptor and $\beta_2$ Adrenoreceptor with comparable affinities and activities. They are thus entirely unsuited for use in the present invention, but they do afford good basis for comparative and competitive binding studies, and are employed in the present invention for those purposes when appropriate.

THE COMPOUNDS OF THE INVENTION

The present invention is based on the provision of $\beta_3$-Adrenoreceptor agonists in pharmaceutically acceptable carrier formulations for administration to stimulate, regulate and modulate metabolism of fats in adipose tissues in animals, particularly humans and other mammals.

The present invention additionally provides a method for safe and effective administration of $\beta_3$-Adrenoreceptor agonists for stimulating, regulating and modulating metabolism of fats in adipose tissues in animals, particularly humans and other mammals.

Compounds which are highly potent and highly specific $\beta_3$-Adrenoreceptor agonists are provided. The compounds are formulated into pharmaceutical preparations and administered for stimulating, regulating and modulating metabolism of fats in adipose tissues in animals, particularly humans and other mammals.

The compounds of the invention have the structure:

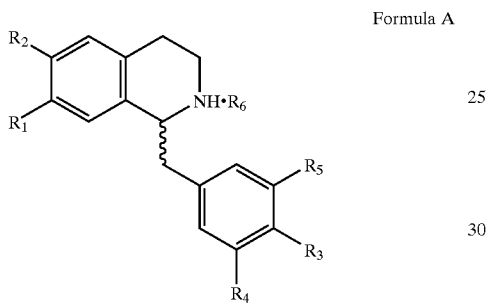

Formula A $R_1$ and $R_2$ are each independently members selected from the group consisting of H, OH, Cl, $NO_2$, $CH_3SO_2NH$, $NH_2$, $CH_3O$ and weak adds of the structure $R_7$—NH, where $R_7$ is an acyl group, wherein at least one of $R_1$ and $R_2$ is OH. It is generally preferred that $R_2$ be OH.

$R_3$, $R_4$ and $R_5$ are variously and independently members selected from I, Br, Cl, F, $OCH_3$, $CH_3$, alkyl, alkylaryl, aminoalkyl, thioalkyl, and O-alkyl. Preferably, R4 and R5 are each a halogen, the same or different.

$R_6$ is an acid moiety which forms an acid salt with the NH group. $R_6$ is desirably HCl or $(COOH)_2$.

While the racemic mixtures are active, selective, and bioavailable, we have found that the isolated isomers are ordinarily of more particular interest. The S(−) isomers are preferred, as they will be found to have the highest selectivity and the highest bioavailability. The R(+) isomers are also effective.

The following are structures of preferred species:

Compound 1

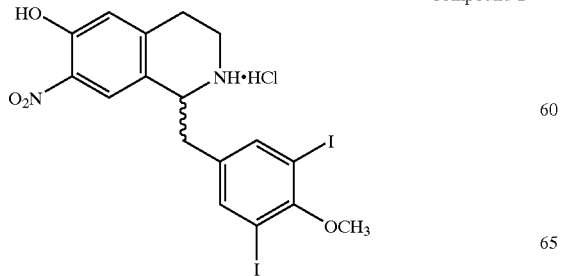

-continued

Compound 2

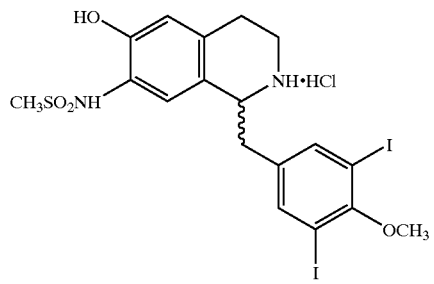

Compound 3

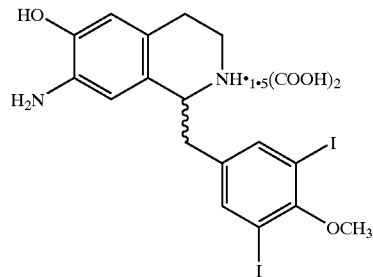

Compound 4

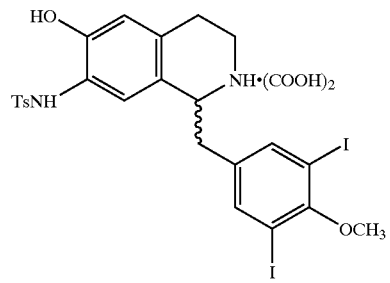

Compound 5

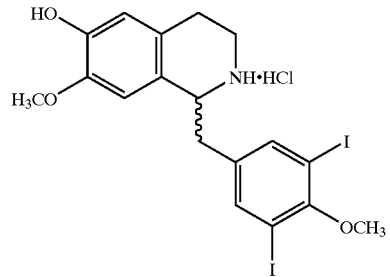

Compound 6

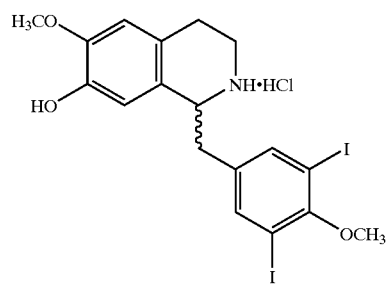

Compound 7

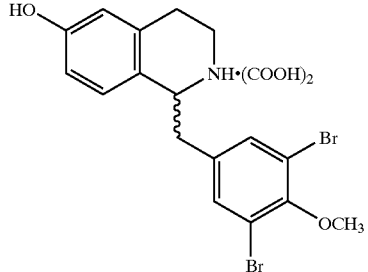

-continued

Compound 8
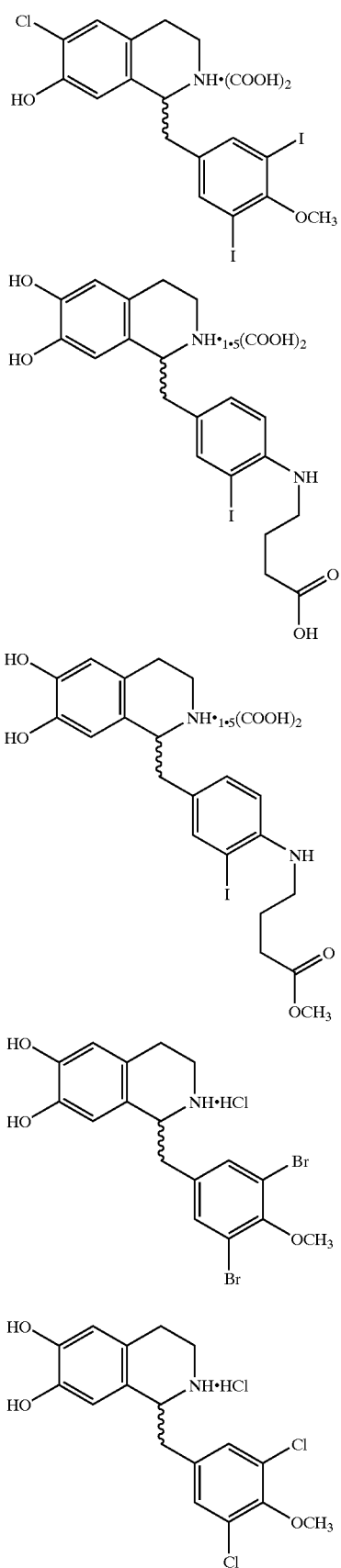
Compound 9

Compound 10

Compound 11

Compound 12

-continued

Compound 13
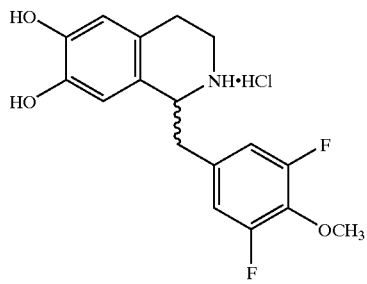

Compound 14
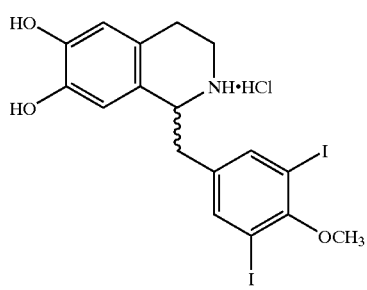

It is preferred that the compounds of the present invention be further qualified and limited to those with high bioavailability, high selectivity and high activity for the $\beta_3$-Adrenoreceptor. In general, selectivity is highest for the S-isomers, and these are generally preferred for these reasons. Thus, preferred species are the following:

Compound 15
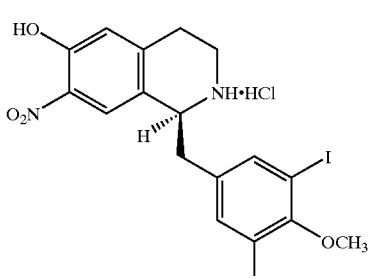

Compound 16
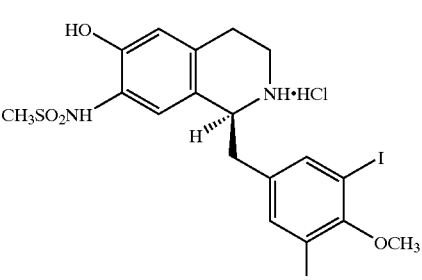

Compound 17
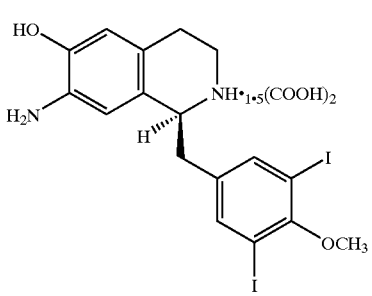

Compound 18
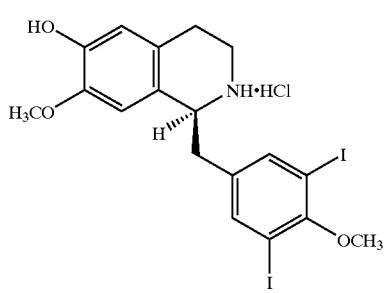
Compound 19
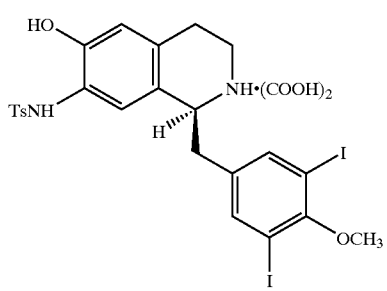
Compound 20
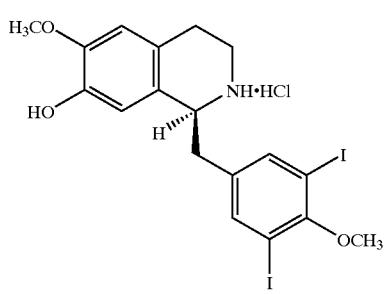
Compound 21
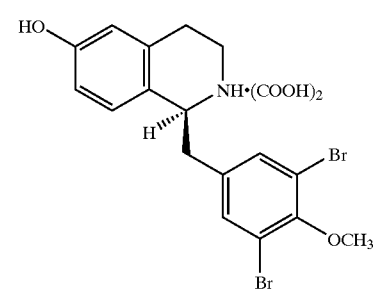
Compound 22
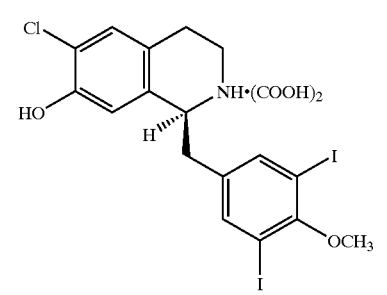
Compound 23
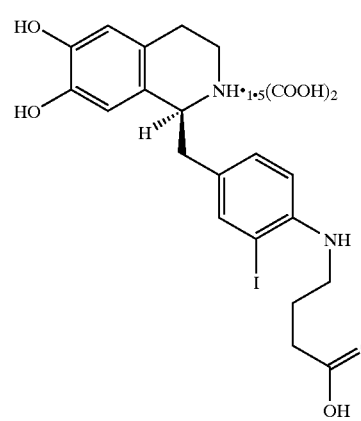
Compound 24
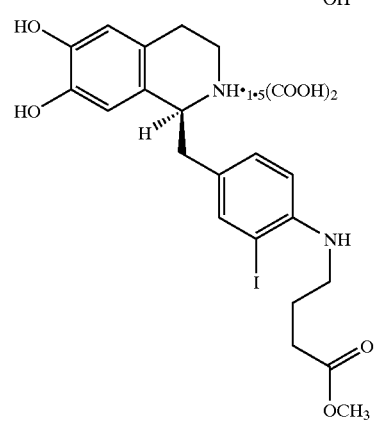
Compound 25
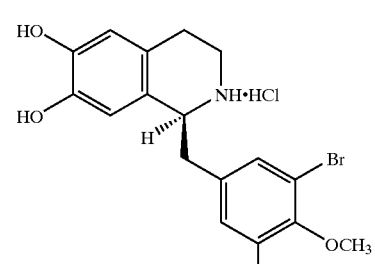
Compound 26
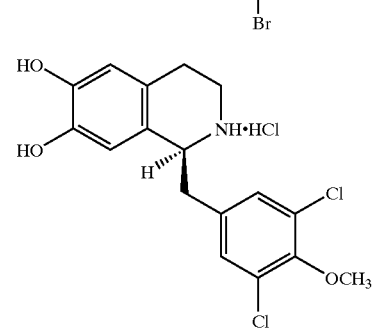
Compound 27
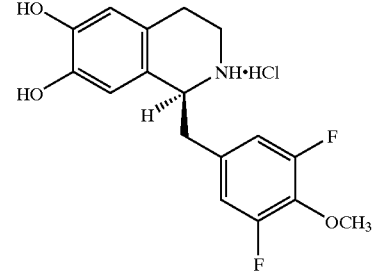

Compound 28
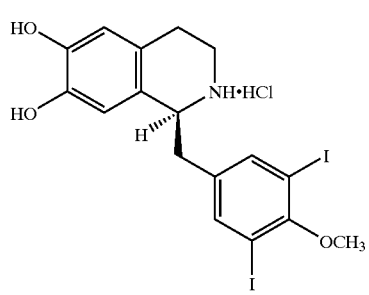
Other species include the following:
Compound 29
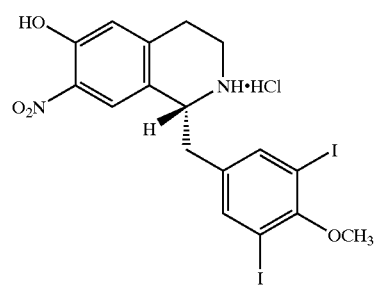
Compound 30
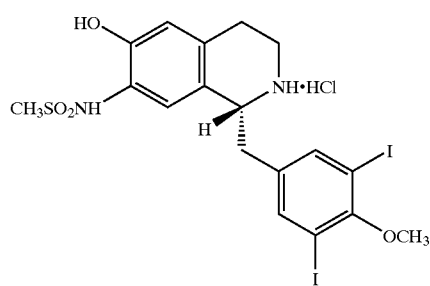
Compound 31
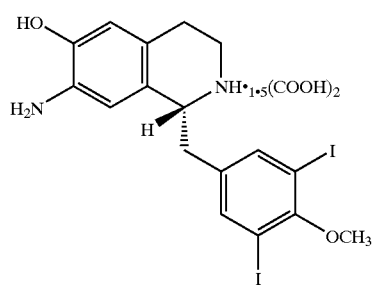
Compound 32
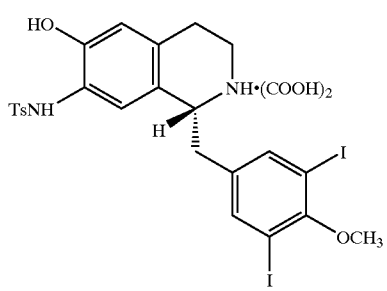
Compound 33
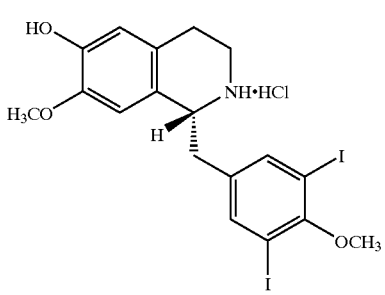
Compound 34
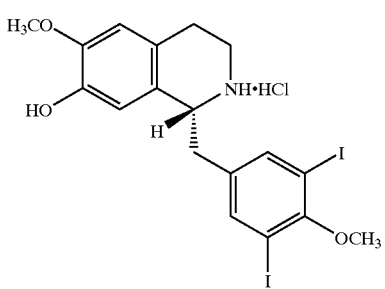
Compound 35
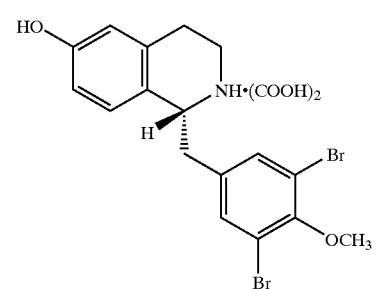
Compound 36
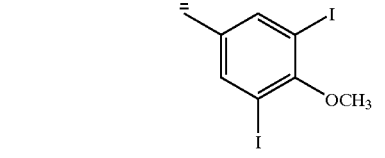
Compound 37
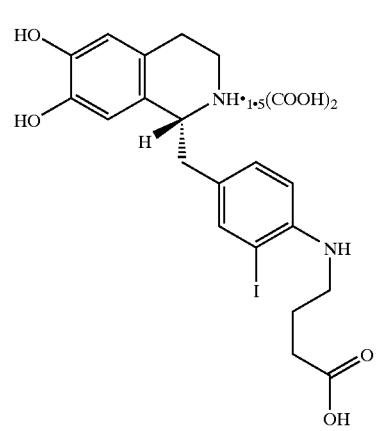

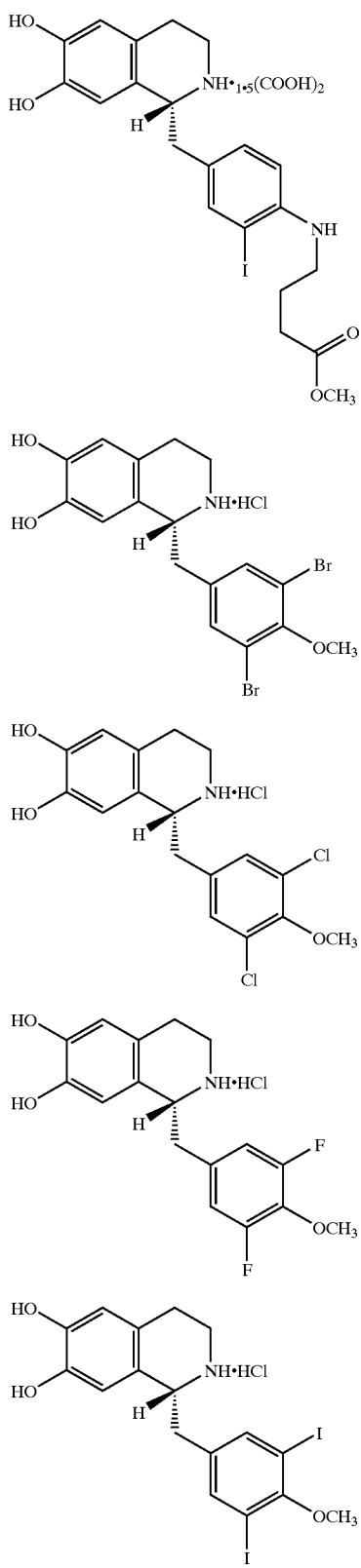
aminoalkyl, thioalkyl, and O-alkyl. Preferably, X and Z are each a halogen, the same or different:
It is particularly desirable to employ compounds of the following structures in the present invention, where moieties X, Y, and Z are are variously and independently members selected from I, Br, Cl, F, OCH3, CH3, alkyl, alkylaryl, Formula B-R

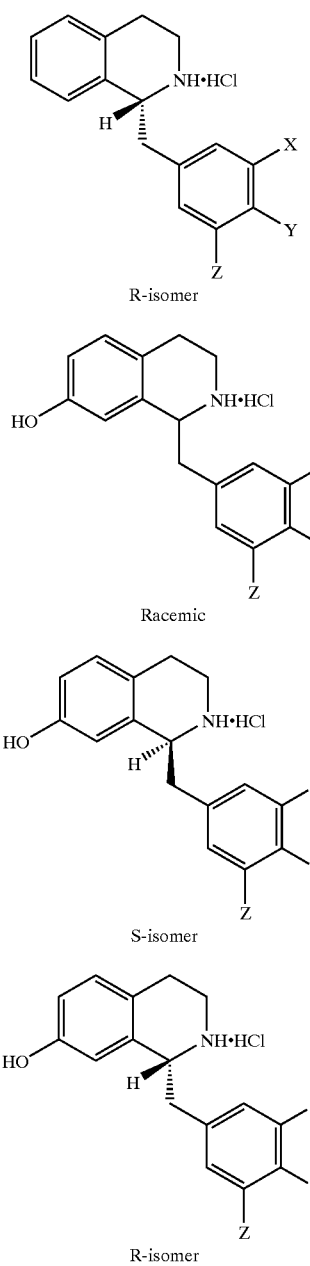

R-isomer

Formula C

Racemic

Formula C-S

S-isomer

Formula C-R

R-isomer

Preferred species of these structures having particularly good properties include the following compounds:

Compound 43

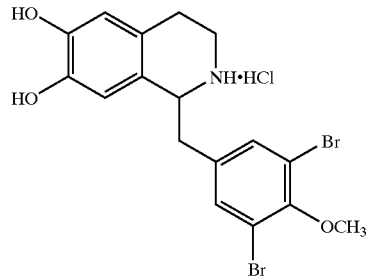

Compound 44

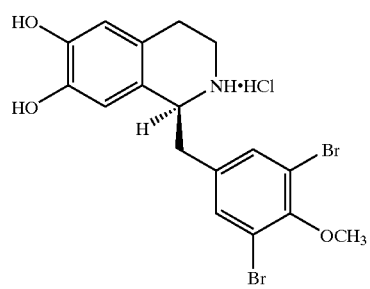

Compound 45

Compound 46

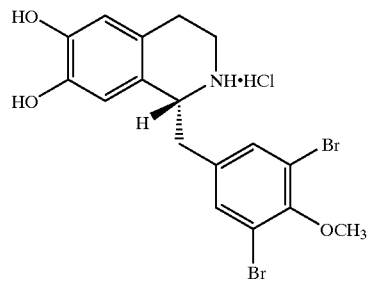

Racemic

Compound 47

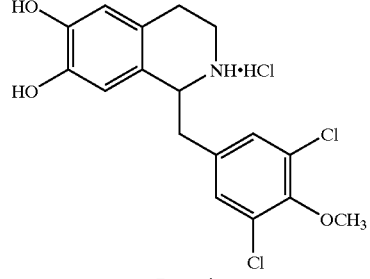

S-isomer

Compound 48

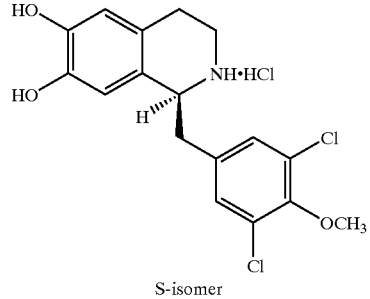

R-isomer

A convenient protection scheme has been devised for the synthesis of the desired $\beta_3$-Adrenoreceptor agonists of the present invention adapted from the procedures disclosed in our prior U.S. application, Ser. No. 09/164,047, which synthesis is hereby incorporated by reference. As those of ordinary skill in the art of chemical synthesis will understand, the procedures there are adapted to the requirements of the present invention by well-known and readily understood adaptations to accommodate selection and use of differing starting reagents. The triple protected isoquinoline intermediates were synthesized as shown in Scheme 1. The tetrahydroisoquinolines 6a–c were synthesized from the O-methyl or O-benzyl protected catecholamines 3a or 3b, respectively, and 4-nitrophenylacetic acid (4a) or 3,5-bis-trifluoromethylphenylacetic acid (4b) using methods described previously. Clark, M. T.; Adejare, A.; Shams, G.; Feller, D. R.; Miller, D. D. "5-fluoro- and 8-fluorotrimetoquinol: selective beta 2-adrenoceptor agonists" *J Med Chem* 1987, 30, 86–90.; Harrold, M. W.; Gerhardt, M. A.; Romstedt, K; Feller, D. R.; Miller, D. D. "Synthesis and platelet antiaggregatory activity of trimetoquinol analogs as endoperoxide/thromboxane A2 antagonists" *Drug Des Deliv* 1987, 1, 193–207. Adejare, A.; Miller, D. D.; Fedyna, J. S.; Ahn, C. H.; Feller, D. R. "Syntheses and beta-adrenergic agonist and antiaggregatory properties of N-substituted trimetoquinol analogues" *J Med Chem* 1986, 29, 1603–9. The amino group of 6a and 6b were protected with trifluoroacetyl (TFA) and t-butyloxycarbonyl (t-BOC), respectively. The nitro groups of 7a,b were reduced via catalytic hydrogenation using Pd/C or Raney Nickel, respectively, to give the aniline derivatives 8a,b. Iodination of 8a,b with 1 equivalent of benzyltrimethylammonium dichloroiodate (BTMACl$_2$I) according to Kajigaeshi et al., Kajigaeshi, S.; Kakinami, H.; Fujisaki, S.; Okamoto, T. "Halogenation using quaternary ammonium polyhalides. VII. Iodination of aromatic amines by use of benzyltrimethylammonium dichloroiodate (I$^-$)" *Bull. Chem. Soc. Jpn.* 1968, 61, 600–602, led to the 3'-iodo analogs 9a,b. An additional 3 equivalents of BTMACl$_2$I added in portions over a 3 day period was required to convert 8a completely to the diiodo derivative 10a.

Isolation of the stereo isomers is performed by known techniques, including recrystallization, column separation using HPLC, adsorption chromotography, and the like.

What is claimed is:

1. A compound having the structure:

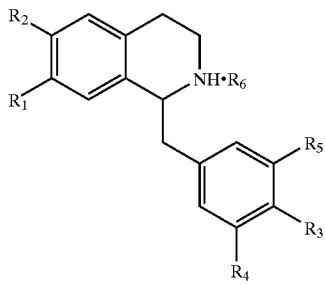

wherein:
one of $R_1$ and $R_2$ is OH and the other is either $R_7$—NH, wherein $R_7$ is an acyl group, or NHS(O)$_2$R, wherein R is alkyl or aryl, or $R_1$ is OH and $R_2$ is NO$_2$ or NH$_2$;

$R_3$, $R_4$, and $R_5$ are each independently selected from the group consisting of hydrogen, halogen, alkyl, alkylaryl, aminoalkyl, thioalkyl, O-alkyl, —NHCH$_2$CH$_2$CH$_2$C(O)OH, and —NHCH$_2$CH$_2$CH$_2$C(O)OCH$_3$; and $R_6$ is an acid moiety that forms an acid salt with the NH group.

2. The compound of claim 1, wherein one of $R_1$ and $R_2$ is NHS(O)$_2$R.

3. The compound of claim 2, wherein R is alkyl.

4. The compound of claim 2, wherein R is aryl.
5. The compound of claim 2, wherein R is tolyl.
6. The compound of claim 2, wherein R is CH$_3$.
7. The compound of claim 2, wherein $R_4$ and $R_5$ are each independently selected halogen.
8. The compound of claim 7, wherein $R_4$ and $R_5$ are bromine.
9. The compound of claim 2, wherein $R_3$ is O-alkyl.
10. The compound of claim 9, wherein $R_3$ is OCH$_3$.
11. The compound of claim 1, wherein $R_1$ is NHS(O)$_2$R.
12. The compound of claim 11, wherein R is alkyl.
13. The compound of claim 11, wherein R is aryl.
14. The compound of claim 11, wherein R is tolyl.
15. The compound of claim 11, wherein R is CH$_3$.
16. The compound of claim 11, wherein $R_4$ and $R_5$ are each independently selected halogen.
17. The compound of claim 16, wherein $R_4$ and $R_5$ are bromine.
18. The compound of claim 11, wherein $R_3$ is O-alkyl.
19. The compound of claim 18, wherein $R_3$ is OCH$_3$.
20. The compound of claim 1, wherein $R_6$ is HCl or (COOH)$_2$.
21. The compound of claim 1, wherein $R_2$ is OH, $R_1$ is NHS(O)$_2$R, $R_4$ and $R_5$ are each independently selected halogen, and $R_3$ is O-alkyl.
22. The compound of claim 21, wherein R is CH$_3$ or tolyl.
23. The compound of claim 21, wherein $R_4$ and $R_5$ are bromine.
24. The compound of claim 21, wherein $R_3$ is OCH$_3$.
25. A pharmaceutical composition, comprising a pharmaceutically acceptable carrier and at least one compound having the structure:

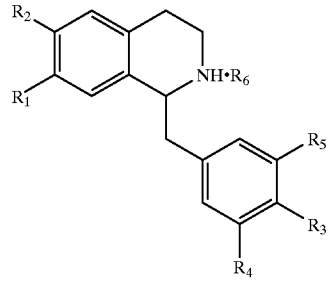

wherein:
one of $R_1$ and $R_2$ is OH and the other is either $R_7$—NH, wherein $R_7$ is an acyl group, or NHS(O)$_2$R, wherein R is alkyl or aryl, or $R_1$ is OH and $R_2$ is NO$_2$ or NH$_2$;

$R_3$, $R_4$, and $R_5$ are each independently selected from the group consisting of hydrogen, halogen, alkyl, alkylaryl, aminoalkyl, thioalkyl, O-alkyl, —NHCH$_2$CH$_2$CH$_2$C(O)OH, and —NHCH$_2$CH$_2$CH$_2$C(O)OCH$_3$; and $R_6$ is an acid moiety that forms an acid salt with the NH group.

26. The pharmaceutical composition of claim 25, wherein one of $R_1$ and $R_2$ is NHS(O)$_2$R.
27. The pharmaceutical composition of claim 26, wherein R is alkyl.
28. The pharmaceutical composition of claim 26, wherein R is aryl.
29. The pharmaceutical composition of claim 26, wherein R is tolyl.
30. The pharmaceutical composition of claim 26, wherein R is CH$_3$.
31. The pharmaceutical composition of claim 26, wherein $R_4$ and $R_5$ are each independently selected halogen.

32. The pharmaceutical composition of claim 31, wherein $R_4$ and $R_5$ are bromine.

33. The pharmaceutical composition of claim 26, wherein $R_3$ is O-alkyl.

34. The pharmaceutical composition of claim 33, wherein $R_3$ is $OCH_3$.

35. The pharmaceutical composition of claim 25, wherein $R_1$ is $NHS(O)_2R$.

36. The pharmaceutical composition of claim 35, wherein R is alkyl.

37. The pharmaceutical composition of claim 35, wherein R is aryl.

38. The pharmaceutical composition of claim 35, wherein R is tolyl.

39. The pharmaceutical composition of claim 35, wherein R is $CH_3$.

40. The pharmaceutical composition of claim 35, wherein $R_4$ and $R_5$ are each independently selected halogen.

41. The pharmaceutical composition of claim 40, wherein $R_4$ and $R_5$ are bromine.

42. The pharmaceutical composition of claim 35, wherein $R_3$ is O-alkyl.

43. The pharmaceutical composition of claim 42, wherein $R_3$ is $OCH_3$.

44. The pharmaceutical composition of claim 25, wherein $R_6$ is HCl or $(COOH)_2$.

45. The pharmaceutical composition of claim 25, wherein $R_2$ is OH, $R_1$ is $NHS(O)_2R$, $R_4$ and $R_5$ are each independently selected halogen, and $R_3$ is O-alkyl.

46. The pharmaceutical composition of claim 45, wherein R is $CH_3$ or tolyl.

47. The pharmaceutical composition of claim 45, wherein $R_4$ and $R_5$ are bromine.

48. The pharmaceutical composition of claim 45, wherein $R_3$ is $OCH_3$.

49. A method for stimulating, regulating and modulating metabolism of fats in adipose tissue in mammals, comprising administering to a mammal an effective amount of a $\beta_3$-adrenoreceptor agonist having the structure:

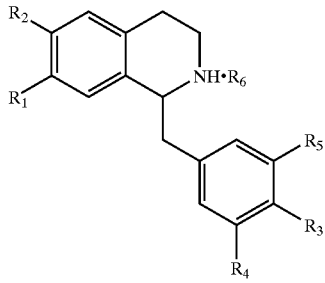

wherein:

one of $R_1$ and $R_2$ is OH and the other is either $R_7$—NH, wherein $R_7$ is an acyl group, or $NHS(O)_2R$, wherein R is alkyl or aryl, or $R_1$ is OH and $R_2$ is $NO_2$ or $NH_2$;

$R_3$, $R_4$, and $R_5$ are each independently selected from the group consisting of hydrogen, halogen, alkyl, alkylaryl, aminoalkyl, thioalkyl, O-alkyl, —$NHCH_2CH_2CH_2C(O)OH$, and —$NHCH_2CH_2CH_2C(O)OCH_3$; and $R_6$ is an acid moiety that forms an acid salt with the NH group.

50. The method of claim 49, wherein one of $R_1$ and $R_2$ is $NHS(O)_2R$.

51. The method of claim 50, wherein R is alkyl.

52. The method of claim 50, wherein R is aryl.

53. The method of claim 50, wherein R is tolyl.

54. The method of claim 50, wherein R is $CH_3$.

55. The method of claim 50, wherein $R_4$ and $R_5$ are each independently selected halogen.

56. The method of claim 55, wherein $R_4$ and $R_5$ are bromine.

57. The method of claim 50, wherein $R_3$ is O-alkyl.

58. The method of claim 57, wherein $R_3$ is $OCH_3$.

59. The method of claim 49, wherein $R_1$ is $NHS(O)_2R$.

60. The method of claim 59, wherein R is alkyl.

61. The method of claim 59, wherein R is aryl.

62. The method of claim 59, wherein R is tolyl.

63. The method of claim 59, wherein R is $CH_3$.

64. The method of claim 59, wherein $R_4$ and $R_5$ are each independently selected halogen.

65. The method of claim 64, wherein $R_4$ and $R_5$ are bromine.

66. The method of claim 59, wherein $R_3$ is O-alkyl.

67. The method of claim 66, wherein $R_3$ is $OCH_3$.

68. The method of claim 49, wherein $R_6$ is HCl or $(COOH)_2$.

69. The method of claim 49, wherein $R_2$ is OH, $R_1$ is $NHS(O)_2R$, $R_4$ and $R_5$ are each independently selected halogen, and $R_3$ is O-alkyl.

70. The method of claim 69, wherein R is $CH_3$ or tolyl.

71. The method of claim 69, wherein $R_4$ and $R_5$ are bromine.

72. The method of claim 69, wherein $R_3$ is $OCH_3$.

73. The method of claim 49, wherein the mammal is a human.

* * * * *